(12) United States Patent
LaCount

(10) Patent No.: US 6,319,717 B1
(45) Date of Patent: Nov. 20, 2001

(54) THERMAL ACID BASE ACCOUNTING IN MINE OVERBURDEN

(76) Inventor: Robert B. LaCount, 403 Arbor Ct., Waynesburg, PA (US) 15370

( * ) Notice: Subject to any disclaimer, the term of this patent is extended or adjusted under 35 U.S.C. 154(b) by 0 days.

(21) Appl. No.: 09/359,754

(22) Filed: Jul. 23, 1999

Related U.S. Application Data

(60) Provisional application No. 60/093,986, filed on Jul. 24, 1998.

(51) Int. Cl.[7] ................................................. G01N 33/24
(52) U.S. Cl. ........................... 436/32; 436/25; 436/26; 436/28; 436/29
(58) Field of Search ........................... 436/32, 29, 34, 436/91, 119, 155, 157; 422/68.1, 78, 82.12, 83, 94, 305, 307

(56) References Cited

U.S. PATENT DOCUMENTS

| | | |
|---|---|---|
| 3,428,433 | 2/1969 | Ehrenberger et al. . |
| 3,784,359 | 1/1974 | Parth . |
| 3,838,972 | 10/1974 | Richards et al. . |
| 3,985,505 | 10/1976 | Bredeweg . |
| 4,011,451 | 3/1977 | Nelson . |
| 4,238,198 | 12/1980 | Swaim et al. . |
| 4,251,727 | 2/1981 | Piercy . |
| 4,635,572 * | 1/1987 | Nickel ................................. 110/344 |
| 4,736,103 | 4/1988 | Nelson et al. . |
| 4,824,790 | 4/1989 | Carangelo et al. . |
| 4,845,040 | 7/1989 | Moon et al. . |
| 4,889,992 | 12/1989 | Hoberman . |
| 5,054,920 | 10/1991 | Doyle . |
| 5,155,019 | 10/1992 | Sussman et al. . |
| 5,204,270 | 4/1993 | LaCount . |
| 5,285,071 | 2/1994 | LaCount . |

FOREIGN PATENT DOCUMENTS

| | | |
|---|---|---|
| 58 195150 | 11/1983 | (JP) . |
| 1 273 792 | 11/1986 | (RU) . |

OTHER PUBLICATIONS

Fletcher "Swelling properties of coal chars during rapid pyrolysis and combustion", Fuel, 1993, 72(11), 1485–95.*

Varnegyi et al. "Mathematical modeling of char reactivity in Ar–O2 and CO2–O2 mixtures", Energy Fuels, 1996, 10(6), 1208–1214.*

LaCount et al., "Coal Characterization by Programmed–Temperature Oxidation," Electric Power Research Institute, pp. 1–13, U.S.A. 1991.

LaCount et al., "Construction and Operation of a Controlled–Atmosphere Programmed–Temperature Reaction Apparatus," Pittsburgh Energy Technology Center, pp. 2–22, U.S.A. 1983.

(List continued on next page.)

Primary Examiner—Jill Warden
Assistant Examiner—Yelena Gakh
(74) Attorney, Agent, or Firm—James Creighton Wray; Meera P. Narasimhan

(57) ABSTRACT

The present invention is a one-step thermal method for analyzing the acid-base content of earth samples, specifically mine overburden samples. By using a low oxygen concentration, preferably about 3%, the transition metal carbonates in the sample decomposed to produce carbon dioxide at a lower temperature than the alkaline earth metal carbonates. In contrast, alkaline earth metal carbonates decompose at approximately the same (higher) temperature regardless of the oxygen concentration. Any oxidizable sulfur forms present in the sample are also oxidized by using this oxygen concentration so that only one experiment is required to obtain the carbonate and sulfur contents of the sample.

26 Claims, 10 Drawing Sheets

OTHER PUBLICATIONS

LaCount et al., "Thermal Oxidative Degradation of Coal as a Route to Sulfur Functionality: An Initial Study," ACS Symposium Series, No. 169, New Approaches in Coal Chemistry, pp. 415–426, U.S.A. 1981.

Stock et al., "Sulfur Distribution in American Bituminous Coals," Energy & Fuels, An American Chemical Society Journal, vol. 3, No. 6, pp. 651–661, U.S.A. 1989.

Friedman, S., "Sulfur Analysis of Coal—A Critical Analysis," Proceedings of the 1990 First International Symposium on the Biological Processing of Coal, Orlando, FL, May 1–3, 1990, pp. 3–12.

LaCount et al., "Sulphur in Coal by Programmed–Temperature Oxidation," American Chemical Society Symposium, New Applications of Analytical Techniques to Fossil Fuels New York City, Apr., 1986. a part of the paper.

IR/FTIR Accessories and Supplies Catalog, Buck Scientific, East Norwalk, CT, Mar., 1990.

Infrared Accessories and Supplies Catalog, Spectra Tech, Stamford, CT, pp. 32–33.

IR/FTIR Catalog, Barnes Analytical/Spectra Tech, Stamford, CT, pp. 6–7.

New Infrared Spectroscopy Supplies Catalog, Perkin–Elmer, PE XPRESS, pp. 26–27.

Calkins, William H., "Investigation of Organic Sulfur–Containing Structures in Coal by Flash Pyrolysis Experiments," Energy & Fuels vol. 1, pp. 59–64, Newark, DE, 1987.

Boudou, J.P. et al., "Identification of Some Sulphur Species in a High Organic Sulphur Coal," Fuel, vol. 66, Nov., 1987, pp. 1558–1569.

Boudou, J.P. et al., "Continuous Gas Detection During Heating of Coal and Kerogen," New Methodologies for Coal Characterization, pp. 1–2, 4–5, France, (undated).

Boudou, J.P., Determination of the Nature of Organic Sulphur in a High Organic Sulphur Coal, International Conference on Coal Science, pp. 13–14, France, 1987.

Fixari, et al. "Oxidative Pyroanalysis: Elemental Analysis in Volatile and Non–Volatile Fractions of Coals and Related, Materials," Fuel, vol. 69, pp. 851–855, France, Jul. 1990.

Warne, S.St.J., "Thermomagnetometry and Evolved Gas Analysis in the Identification of Organic and Pyritic Sulphur in Coal and Oil Shale," Proceedings of ICTA 1985, Bratislava, Thermochimica Acta, vol. 93, pp. 745–748.

Solomon, R.P., "Analysis of the Argonne Premium Coal Samples by Thermogravimetric Fourier Transform Infrared Spectroscopy," Energy & Fuels, vol. 4, No. 3, 1990, pp. 319–333.

Carangelo, Robert M. et al., "Application of TG–FT–i.r. to Study Hydrocarbon Structure and Kinetics," Fuel, vol. 66, Jul. 1987, pp. 960–967.

Carangelo, R.M. et al., "Quantitative Evolved Gas Analysis From An Indianhead Zap Lignite," TG/PLUS Application Note, Advanced Fuel Research, Hartford, CT.

Whelan, Jean K. et al., "Thermogravimetric Fourier Transform Infrared Spectroscopy (TG–FTIR) of Petroleum Source Rocks. Initial Results," Energy & Fuels, vol. 2, No. 1, 1988, pp. 65–73.

Hammack, Richard W., "Evolved–Gas Analysis: A Method for Determining Pyrite, Marcasite, and Alkaline–Earth Carbonates,"Environmental Geochemistry of Sulfide Oxidation, Pittsburgh Research Center, Sep. 1993, pp. 431–444.

Skousen, J. et al., "Neutralization Potential of Overburden Samples Containing Siderite," Journal of Environmental Quality, vol. 26, No. 3, May–Jun. 1997, pp. 673–681.

Hammack, Richard W., "Evolved Gas Analysis—A New Method for Determining Pyrite, Bicarbonate, and Alkaline Earth Carbonates," Proceedings of the Eighth Annual West Virginia Surface Mine Drainage Task Force Symposium, Apr. 7–8, 1987.

LaCount, R.B. et al., "Metal Sulfide Contenet of Ore Samples Determined by Controlled–Atmosphere Programmed–Temperature Oxidation (CAPTO)," Proceedings of an International Biohydrometallurgy Symposium, Aug. 22–25, 1993, Jackson Hole, WY, pp. 665–672.

Lapakko, Kim, "Mine Waste Drainage Quality Prediction: A Literature Review," Minnesota Department of Natural Resources, 1991, pp. 2–49.

Brady, Keith B.C. et al., "A Manual for Premining Prediction of Coal Mine Drainage Quality," Commonwealth of Pennsylvania, Department of Environmental Resources, pp. 1–56.

Brady, Keith B.C. et al., Evaluation of Acid–Base Accounting to Predict the Quality of Drainage at Surface Coal Mines in Pensylvannia, Proceedings of International Land Reclamation and Mine Drainage Conference and The Third International Conference on the Abatement of Acidic Draining, vol. 1, Mine Drainage—SP 06A–94, Pittsburgh, PA, Apr. 24–29, 1994, pp. 138–147.

Smith, Michael W. and Brady, Keith B.C., "Evaluation of Acid Base Accounting Data Using Computer Spreadsheets," Proceedings of the 1990 Mining and Reclamation Conference and Exibition, Apr. 23–26, 1990, Charleston, WV, pp. 213–219.

Leavitt, Bruce et al., "Effects of Siderite on the Nuetralization Potential in the Acid–Base Account," Proceedings of the Sixteenth Annual West Virginia Surface Mine Drainage task Force Symposium, Apr. 4–5, 1995, Morgantown, WV.

Hammack, Richard W. et al., "Methods for Determining Fundamental Chemical Differences Between Iron Disulfides From Different Geologic Provenances," Bureau of Mines Information Circular, vol. 1: Mine Water and Mine Waste, 1988, pp. 136–146.

An Overview of the Controlled–Atmosphere Programmed–Temerature Oxidation (CAPTO) Materials Characterization Method, ViRoLac Industries product literature.

CAPTO Application: Coal Analysis, ViRoLac Industries information brochure.

CAPTO® : Materials Characterization, excerpt from ViRoLac News vol. 1, Winter 1994.

Wert, Charles A. et al., "Applications of Transmission Electron Microscopy to Coal Chemistry," Paper presented at the American Chemical Society Symposium—New Applications of Analytical Techniques to Fossil Fuels, New York City, Apr. 1986.

* cited by examiner

THERMAL ACID BASE ACCOUNTING IN MINE OVERBURDEN

This application claims the benefit of U.S. Provisional Application No. 60/093,986, filed Jul. 24, 1998.

BACKGROUND OF THE INVENTION

Acreage to undergo surface coal mining requires a permit to ensure that mining will not create an environmental waste drainage problem. The site must be tested using an acid-base accounting (ABA) method for prediction of post mining water quality. Current methods may overestimate the potential acidity or alkalinity depending on the components present in the overburden. Needs exist for the development of an improved ABA method for analysis of coal mine overburden. U.S. Pat. Nos. 5,204,270 and 5,285,071 are incorporated herein by reference.

The existing methods compare total potential acidity and alkalinity. If the comparison shows an expected acid drainage, the mine is not permitted to be established.

The current acid accounting method involves prediction of total acidity based on analysis of the total sulfur content and assumes that all sulfur will be converted to sulfate with a corresponding production of acid.

The present base accounting method involves prediction of total alkalinity based on analysis of total carbonate and assumes that the neutralizing effect of all carbonates will be realized.

Recent work has been completed to compare "improved" variations of wet chemical back titration methods to obtain a neutralization potential for mine overburdens. These methods were evaluated in a recent journal article "Neutralization Potential of Overburden Samples Containing Siderite" by J. Skousen et al. in the Journal of Environmental Quality, Volume 26, no. 3, May–June, 1997 which compared the results of 31 samples all analyzed by three different laboratories. The methods include (1) the Sobek method, (2) a method where the sample is boiled for 5 minutes, (3) a method similar to (2) but includes a filter step and treatment with hydrogen peroxide before back titration, and (4) a modified Sobek method that includes the addition of hydrogen peroxide after the first hand titration. The results showed wide variation in neutralization potential among the four methods used and among the three laboratories producing the results. Clearly, a better method is required and will be welcomed by the agencies requiring these tests.

All sulfur forms in overburden do not contribute to acidity upon weathering. Predicting acidity based on the total sulfur content may result in a higher value than the real acidity, denial of many mining permits, and the loss of jobs.

All metal carbonates found in overburdens do not contribute to an overall neutralizing effect of acids. Use of total carbonate content may overestimate the overburden neutralizing capacity. This has resulted in mining permits being denied in cases where the acidity/alkalinity are too close to predict drainage quality. A better ABA method may open some of this acreage for mining.

The Department of Energy (DOE) is interested in a thermal method for analysis of overburden. Work toward a method is described in a paper entitled "Evolved Gas Analysis—A Method for Determining Pyrite, Marcasite, and Alkaline Earth Carbonates" by Hammack in Proceedings: 204th National Meeting of the ACS, Wash. D.C., Aug. 23–28, 1992 and a paper entitled "Evolved Gas Analysis—A New Method for Determining Pyrite, Bicarbonate, and Alkaline Earth Carbonates by Hammack in Proceedings of the Eighth Annual West Virginia Surface Mine Drainage Task Force Symposium, Apr. 7–8, 1987. Under those conditions any siderite (iron carbonate) present would have decomposed with the calcite (calcium carbonate) and dolomite (calcium magnesium carbonate). The work did not include siderite. However, the papers did show overlap between the decomposition temperatures of rhodochrosite and calcite.

The new thermal approach, described in this application, is being used to analyze some overburden samples that are of interest to Hammack at the DOE Federal Energy Technology Center.

SUMMARY OF THE INVENTION

The invention provides a new ABA one-step thermal analytical method. The amount of sulfur dioxide produced from an overburden sample as each sulfur form is thermally oxidized or decomposed is correlated with the leachable acid content. The carbon dioxide evolving from decomposition or oxidation of each carbon form in the overburden sample is determined from the same experiment and correlated with alkalinity.

Only the sulfur forms known to contribute to leachable acidity and the carbon forms contributing to overall alkalinity are compared to determine potential acidity/alkalinity of overburden. This invention results in a significantly improved ABA method for mine overburden material. Various thermal instrument manufacturers may modify instruments to use the new method.

The inventor's previous two patents relate to development of a Controlled-Atmosphere Programmed-Temperature Oxidation (CAPTO) instrument/method for use as a tool to facilitate optimization of parameters for coal analyses, new coal upgrading technologies under study, and to solve challenging analytical problems that arise in the coal and a variety of other industries. CAPTO is used to characterize the thermal oxidation of mineral sulfides and decomposition of sulfates and carbonates. The work is modified to include siderite and rhodochrosite along with calcite and dolomite. This work has led to an inexpensive method capable of predicting the acid and base content being leached from mine overburden samples. Using a 3% oxygen/97% inert gas mixture and one determination per sample, the invention identifies the sulfur forms and the carbonates as a route to quantitatively predict the acid/base potential of the overburdens.

The present invention is important. The normal neutralization potential (for carbonate) and sulfur forms acidity predictions (for pyrite and sulfate) may overestimate the base/acid accounting for an overburden sample. Actual leaching tests that may provide a reliable prediction of the acidity/basicity to be realized from an overburden sample require a lengthy leach period (approximately 10 weeks) and cost approximately 3–4 times as much as the thermal method described below. However, no standard leaching reference method has been established, possibly due to the cost of the analyses.

Understanding the characteristics of thermal oxidation/decomposition of sulfides/sulfates-carbonates leads to a better estimate of the acidic/alkaline weathering potential of strata. This application permits a more accurate prediction of acidic mine drainage from the overburden and enables mine operators to plan their mining and reclamation operations accordingly. The test results for acid discharge potential that now must accompany each new mine permit application tend either to overestimate the acidic/alkaline potential of strata above and below the coal bed or require lengthy real-time leach analysis.

The total carbonate content of an overburden sample that contains transition metal carbonates such as iron or manganese carbonates and alkaline earth metal carbonates such as calcium carbonate and dolomite are not realized in an actual leaching experiment since only the calcium carbonate and dolomite readily leaches or contributes to an overall neutralizing effect of acids. Likewise, if an overburden that contains pyrite, iron sulfate, and calcium sulfate were analyzed for sulfur content and related to acidity, the potential acidity would be overestimated, since calcium sulfate contributes little to potential acidity.

If the total inorganic sulfur content and, therefore, the potential acidity is high in an overburden sample, a mining permit may not be issued without extensive and expensive leaching studies. However, if much of the sulfur is present as calcium sulfate, only a fraction of the potential acidity will be realized and the mine could have been permitted. Similarly, if the potential basicity is greater than the potential acidity a mining permit may be issued. However, if much of the carbonate present occurs as iron or manganese carbonate, a mine acid drainage problem may arise since most of the carbonate neutralization potential from these carbonates will not be realized.

The thermal analytical method developed to solve this problem is based on the following:

(1) Identifying any changes in thermal decomposition behavior of metal carbonates with variation in the gas or gas composition passing through the sample as the sample is heated from some lower temperature to beyond its decomposition point.

(2) Identifying gas compositions and the proper temperatures for changing gas compositions, if necessary, consistent with obtaining well resolved sulfur dioxide evolutions produced from metal sulfides, sulfates, and hydroxy sulfates found in the overburden samples. A knowledge of the thermal oxidation behavior of metal sulfides, the thermal decomposition of metal sulfates, and any hydroxy or complex sulfates present in overburden samples is required. This same information with respect to variation in the gas or gas composition passing through the sample as it is heated through the same temperature regime is required for method development.

For example, jarosites decompose to produce sulfur dioxide above 500° C. under oxidation conditions but show no sulfur dioxide evolution up to 1050° C. under inert gas conditions. If the sample previously exposed to inert gas conditions up to 1050° C. is treated again under oxidizing conditions, the characteristic decomposition and sulfur dioxide evolution above 500° C. is not observed. Thus, oxidizing conditions are required to obtain a reliable estimate of some sulfur forms through a thermal oxidation/decomposition procedure. The method may require changes in gas or gas composition throughout the temperature regime if both sulfur forms and carbonate are to be reliably estimated from one determination.

(3) Identifying gas compositions and the proper temperatures for changing gas compositions (if necessary) in order to obtain well resolved carbon dioxide evolutions produced from metal carbonates present in the overburden samples is required for a successful method. For example, the carbon dioxide evolutions produced from iron carbonate and calcium carbonate decomposition in pure oxygen occur as severely overlapping peaks. This overlap of the carbon dioxide evolutions from the metal carbonates makes quantitative determinations difficult and non-reproducible, and has deterred development of a one-step thermal analytical method for analysis of these carbonates. However, a thermal study of iron carbonate and calcium carbonate under differing gas concentrations shows variation in decomposition temperatures (rates) and permits utilization of a quantitative thermal analytical method for the analysis.

Under inert gas or low oxygen conditions iron or manganese carbonate decomposes to produce carbon dioxide at a lower temperature and over a smaller temperature range than that produced under oxidative conditions. However, calcium carbonate or dolomite decomposes under oxidative or inert gas conditions at approximately the same temperature.

Previous examination of the thermal oxidation/decomposition of sulfides/sulfates using a variety of oxygen/inert gas concentrations revealed a trend of pyrite to oxidize at lower temperature as the oxygen concentration decreased. Use of this information coupled with the current determinations of the thermal behavior of iron and manganese carbonates, calcium carbonate, dolomite, jarosites, and the other sulfates permit a thermal, one-step, direct determination of the acidity/basicity likely to result from an overburden sample.

An overburden sample temperature-programmed thermal analysis is completed initially using a low concentration of oxygen passing through the sample to promote oxidation of pyrite at as low a temperature as possible. The analysis is continued by use of an inert gas throughout the decomposition temperature range of iron carbonate, if necessary. The gas flow is then switched back to an oxidative atmosphere (if it is not already an oxidative atmosphere) prior to decomposition of sulfur forms such as jarosite and alkaline earth carbonates. This method provides well-resolved easily quantified carbon dioxide evolutions for iron carbonate, manganese carbonate, calcium carbonate, and dolomite as well as well-resolved easily quantified sulfur dioxide evolutions for the sulfur forms present in the overburden samples. Working with the pure iron carbonate and calcium carbonate, for example, one would expect to have to go through their decomposition temperature range using inert gas or a low oxygen concentration. However, on the real overburden samples, 3% oxygen appears to give good resolution between the siderite and calcium carbonate and provides an adequate supply of oxygen for oxidation of the sulfur forms.

Experimental work has shown why the decomposition temperatures of transition metal carbonates such as siderite and rhodochrosite and alkaline earth carbonates such as calcite and dolomite present in actual overburden samples may be better separated or resolved than mixtures of the authentic transition metal and alkaline earth carbonates. Authentic transition metal carbonates, for example, siderite and rhodochrosite may be made to undergo thermal decomposition at a lower temperature similar to that observed in most overburdens if a material, for example, kaolinite is thoroughly mixed with the analysis sample prior to analysis. Kaolinite evolves moisture throughout the temperature range where rhodochrosite, siderite, calcite, and dolomite thermally decompose to produce carbon dioxide. The presence of water vapor obtained insitu as the sample undergoes thermal analysis produces an effect that causes the transition metal carbonates (for example, rhodochrosite and siderite) to decompose and evolve carbon dioxide at a temperature lower than that observed when compared to a sample analyzed containing no added material, for example, kaolinite. If kaolinite is heated to a temperature above that of the decomposition temperature of the components of the mixture being analyzed, for example, 800° C. or beyond in this case to remove water, and then mixed with a sample containing transition metal carbonates, the thermal decomposition of the transition metal carbonates occurs at the same temperatures observed when no kaolinite was added to the mixture analyzed.

The capability to change the decomposition temperature of some components in a sample undergoing thermal analysis to produce well-resolved thermal decomposition temperatures for the components to be analyzed is an important feature of this invention that results in an improved ABA method when an overburden sample contains little or no clay. Decomposition temperature may be changed by several different methods: (1) changing the fluid flowing through the sample to a different fluid; (2) changing the composition of a fluid mixture flowing through the sample; (3) admixture of a substance to the sample mixture prior to thermal analysis; and (4) admixture of a substance to the sample mixture prior to thermal analysis that produces another substance insitu during thermal analysis.

This invention methodology forms a basis for thermally analyzing the components of sample mixtures that may decompose at similar temperatures under one given set of thermal analysis parameters but decomposes at different and unforeseeable temperatures by use of one of the aforementioned methods (items 1–4 in the preceding paragraph).

The invention includes three scenarios for use of fluids flowing through the sample being analyzed. First, an inert gas temperature-programmed thermal analysis to obtain the amount of carbonate available for neutralization and a second temperature-programmed thermal analysis under oxidative conditions to obtain the sulfur forms results.

Second is gas switching, as described above. The method is initially oxidative to oxidize the lower sulfur forms, switching to inert gas as the temperature goes through the transition metal carbonate decomposition range, and switching back to oxidative as soon as the transition metal carbonates are decomposed to analyze the higher decomposition temperature alkaline earth metal carbonates and sulfur forms.

Last, and the preferred method, is use of some low concentration of oxygen, such as 3%, in a temperature-programmed thermal analysis that provides for oxidation/decomposition of the sulfur forms and still provides good resolution between transition metal and alkaline earth carbonates, for example, siderite and calcite decomposition temperatures. Other concentrations of oxygen, for example 0–100%, may result in well-separated thermal decomposition temperatures of the transition metal and alkaline earth carbonates when certain substances, for example, kaolinite are present in or are added to the sample to be analyzed. The invention includes the method of adding a substance to the analysis sample to change the thermal oxidation/decomposition temperature of some of the components present in the sample. Admixture of certain materials, for example, kaolinite to a sample followed by temperature-programmed thermal analysis causes transition metal carbonates to react/decompose at a temperature lower than that observed with no added materials present. Addition of kaolinite to an analysis sample evolves water insitu during the temperature-programmed thermal analysis and causes a greater shift in decomposition temperature to lower temperatures for transition metal carbonates, for example siderite and rhodochrosite, compared to alkaline earth carbonates, for example, calcite and dolomite.

The temperature and concentration of supplied gas and gas switching are under computer control when CAPTO is used as the instrument for completing the analysis.

These and further and other objects and features of the invention are apparent in the disclosure, which indicates the above and ongoing written specification, with the claims and the drawings.

DETAILED DESCRIPTION OF THE PREFERRED EMBODIMENTS

FIGS. 1–4 show examples of several actual analyses of samples showing sample numbers and calculations of amounts present. The overburden samples show carbonate decompositions at somewhat different temperatures than the pure components. However, both decomposition temperature shifts are in the same direction and the resolution between peaks is very good. This is likely due to matrix effects of the other components in the overburden sample.

Figure 1:
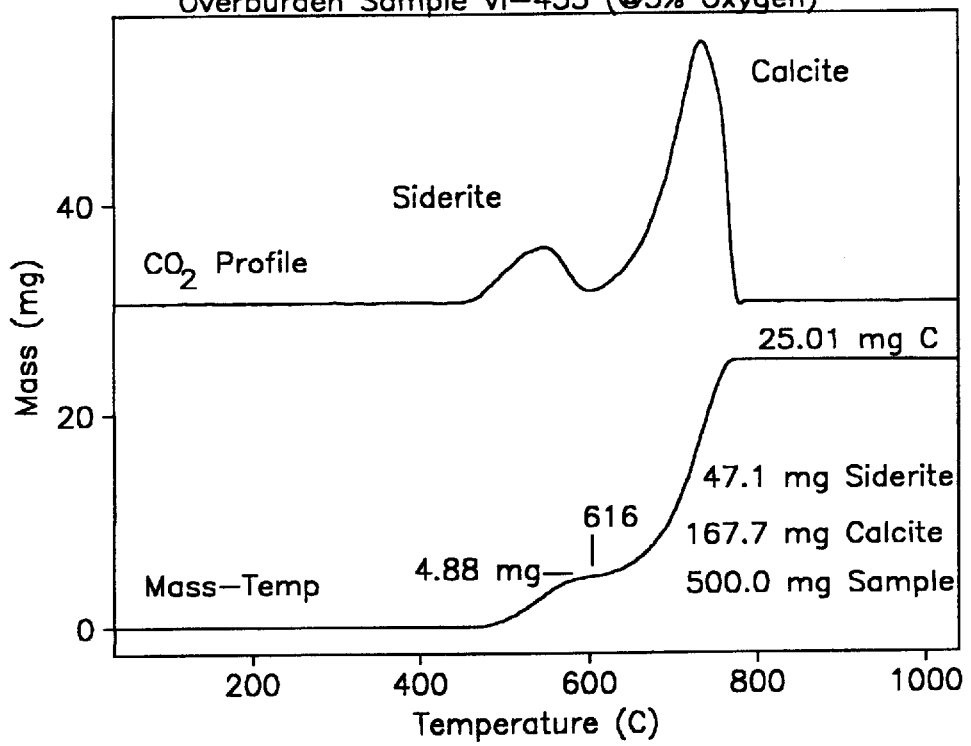
FIG. 1 shows the carbon dioxide profile and mass-temperature plot of overburden sample VI-433 at 3% oxygen.
Figure 2:
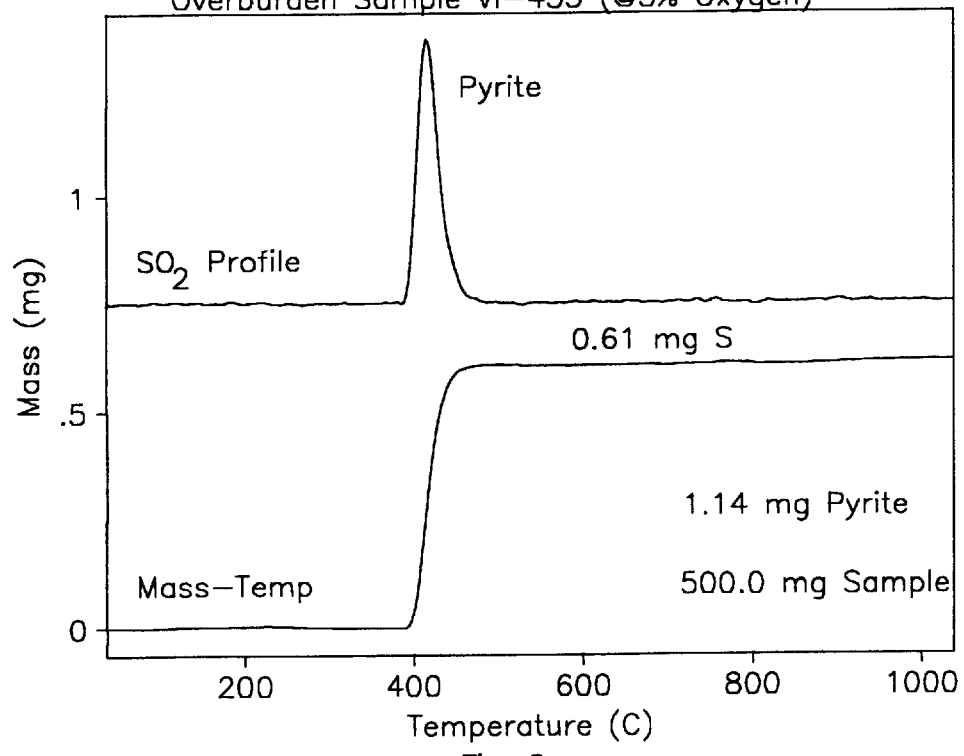
FIG. 2 shows the sulfur dioxide profile and mass-temperature plot of overburden sample VI-433 at 3% oxygen.
Figure 3:
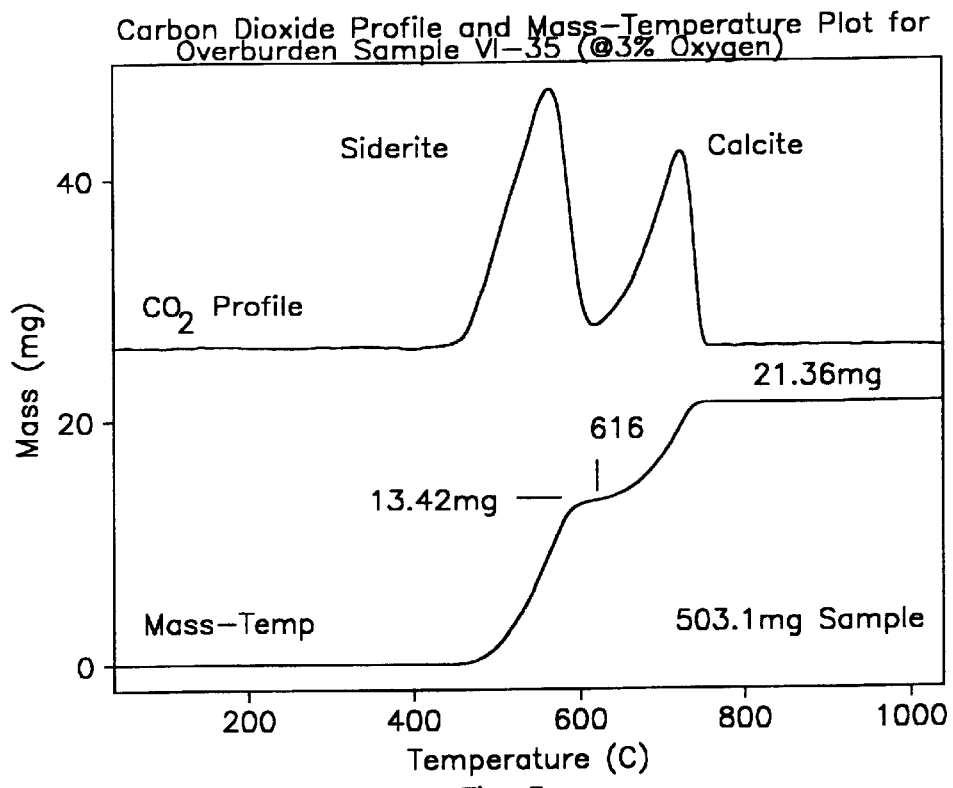
FIG. 3 shows the carbon dioxide profile and mass-temperature plot of overburden sample VI-35 at 3% oxygen.
Figure 4:
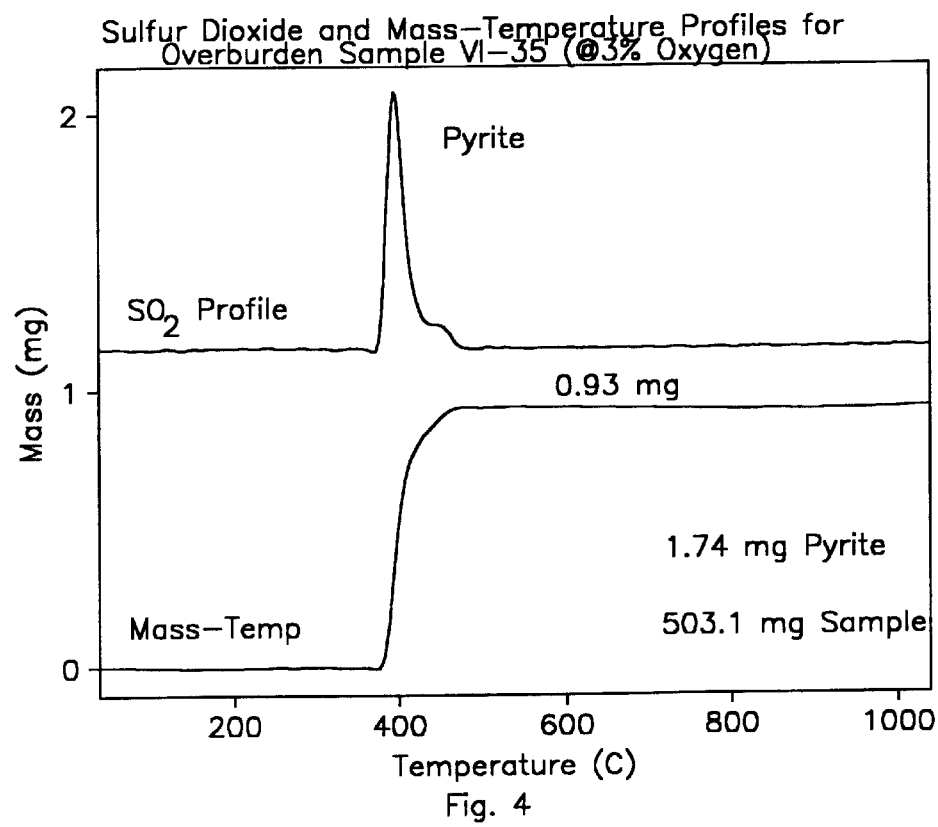
FIG. 4 shows the sulfur dioxide profile and mass-temperature plot of overburden sample VI-35 at 3% oxygen.
Figure 5:
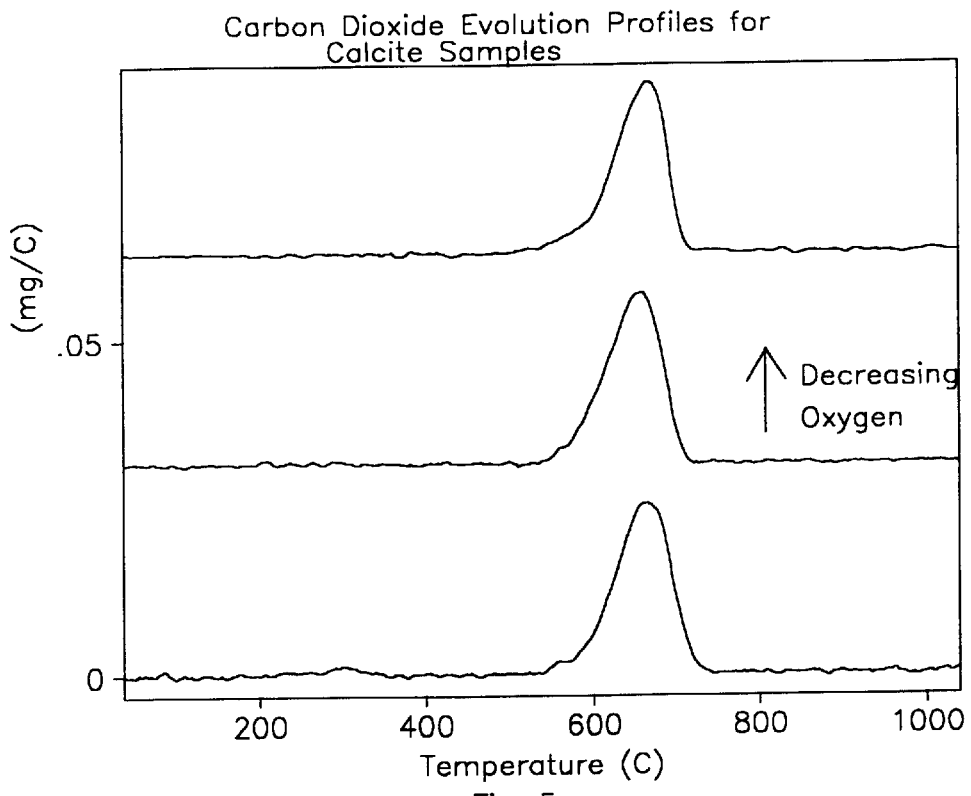
FIG. 5 shows the carbon dioxide profiles for calcite thermally decomposed using different oxygen-inert gas concentrations.
Figure 6:
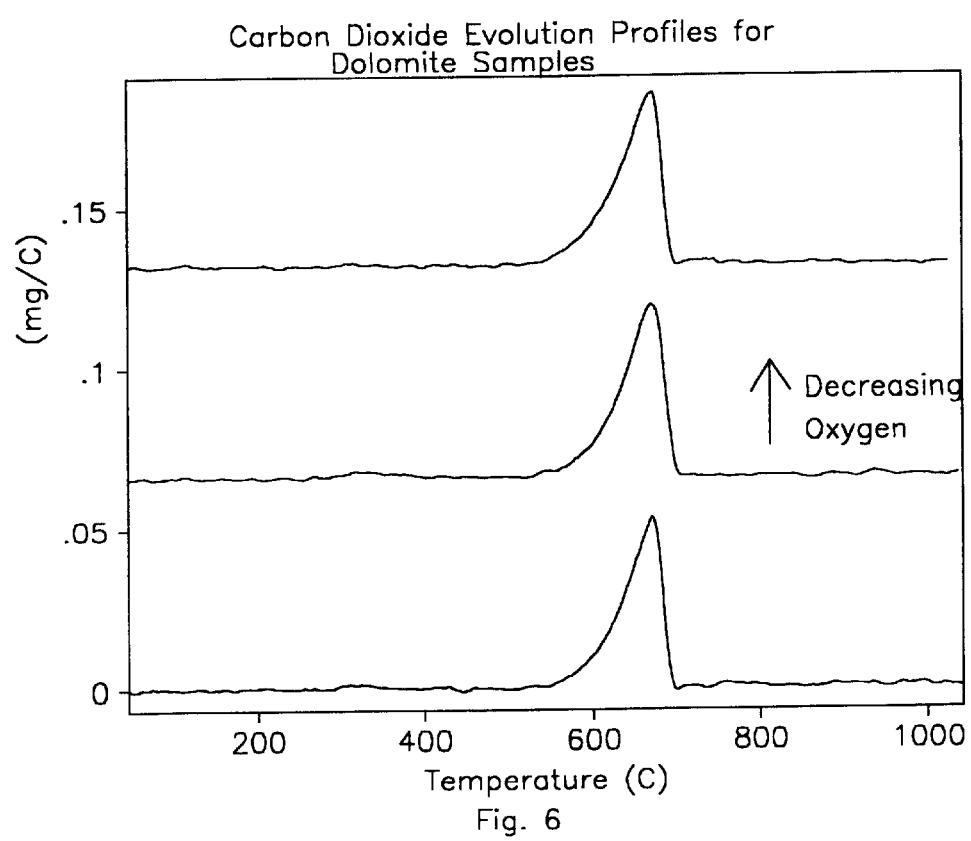
FIG. 6 shows the carbon dioxide profiles for dolomite thermally decomposed using different oxygen-inert gas concentrations.
Figure 7:
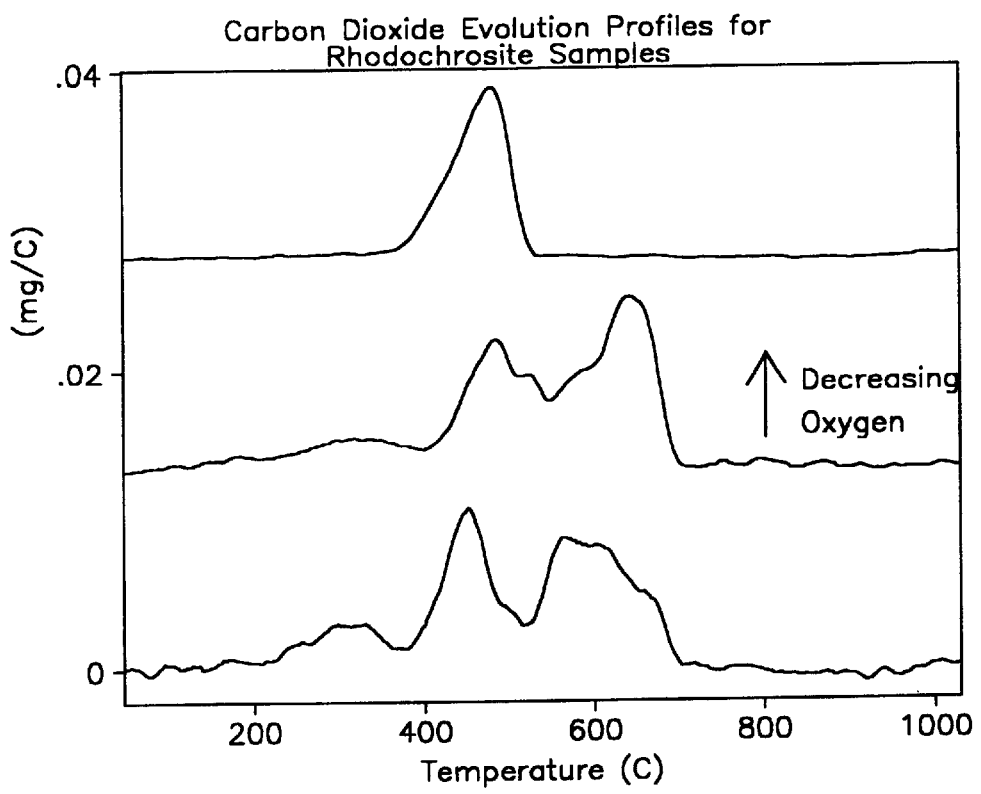
FIG. 7 shows the carbon dioxide profiles for rhodochrosite thermally decomposed using different oxygen-inert gas concentrations.
Figure 8:
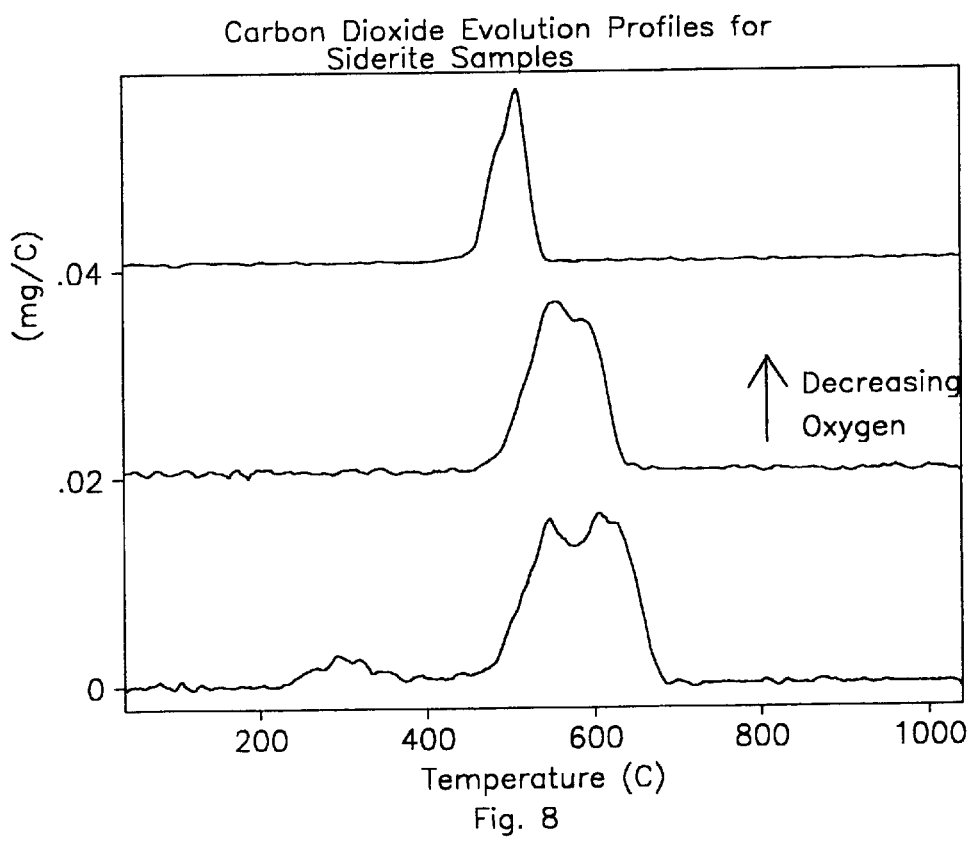
FIG. 8 shows the carbon dioxide profiles for siderite thermally decomposed using different oxygen-inert gas concentrations.

Results show some temperature shifts in the carbonate decomposition peaks from overburden to overburden. However, in these cases both peaks are shifted in the same direction and the resolution between peaks is still very good. These effects are simple matrix effects due to the different makeup of the other components in the overburdens. Actually, it would be surprising not to see these effects. The resolution between the siderite and the calcite in these overburden samples is good even with an oxygen content as high as 3%. The resolution between peaks is better than the pure components that were examined at 3% oxygen. FIGS. 2 and 4 show sulfur dioxide evolution produced from pyrite oxidation occurring in these samples in a rather sharp peak just over 400° C. as expected. The peak is well defined indicating that adequate oxygen is present in the gas stream for oxidation of the pyrite in these overburden samples. The small sulfur dioxide evolution in FIG. 4 near 440° C. is due to the presence of a second type of pyrite present in some overburden samples. Note that these overburden samples are free of various sulfates that decompose at specific temperatures different from and above the pyrite oxidation temperature.

FIGS. 5–8 show the trend in thermal decomposition behavior of calcite, dolomite, rhodochrosite, and siderite under three selected oxygen-inert gas concentrations. The same three selected oxygen-inert gas concentrations were used with each different carbonate examined (i.e., FIGS. 5 through 8). Note that the thermal decomposition temperature of the alkaline earth metal carbonates calcite and dolomite are similar and show little or no change in thermal decomposition temperature as the oxygen concentration is decreased. Contrast that behavior to the transition metal carbonates rhodochrosite and siderite. Under high oxygen concentration these transition metal carbonates begin to decompose before 300° C. and continue to decompose until nearly 700° C. As the oxygen concentration is decreased the main decomposition temperature shifts to a lower temperature and the decomposition temperature range narrows. Under low oxygen concentration the decomposition temperature of rhodochrosite and siderite is lower than and well separated from that of calcite or dolomite. This difference in decomposition trends between the alkaline earth metal carbonates and the transition metal carbonates forms the basis of a method for analysis of mixtures of these two classes of carbonates present in mine overburdens. The overburdens may be effectively analyzed for transition metal carbonates, alkaline earth carbonates (no overlap of decomposition temperatures), and sulfur forms using low concentrations of oxygen, for example, 3% oxygen in nitrogen, argon or other inert gas. Concentrations of oxygen in inert gas may range from 0% up to 5%. Even as high as 10% oxygen provides some separation of the authentic transition metal carbonates from the authentic alkaline earth metal carbonates (partial overlap of decomposition temperatures at 10% oxygen) and even better separation of these components in an actual overburden sample is realized under these conditions. The optimum selection of oxygen concentration for this one-step method is that which provides the least overlap between the decomposition temperature of the transition metal carbonates and the alkaline earth metal carbonates and provides adequate oxygen to oxidize sulfur forms present for a wide range of mine overburden samples. A variety of different mine overburdens have been studied to ascertain the optimum oxygen concentration for the analysis. If a substance that releases water over the thermal analysis temperature of interest, such as kaolinite, is present in or added to the sample to be analyzed or if low levels of water vapor are added to the supplied gas stream, any concentration of oxygen that is sufficient to oxidize the sulfur forms present may be used as well as concentrations up to 100% oxygen and the decomposition profiles of the transition metal carbonates, such as siderite and rhodochrosite, are well resolved from the alkaline earth carbonates, such as calcite and dolomite. A method for the selective analysis of these two classes of carbonates in mine overburden is important since the alkaline earth metal carbonates have an overall acid neutralizing effect and the transition metal carbonates do not contribute an overall acid neutralizing effect. Using the present invention, it is now possible to analyze for and subtract the transition metal carbonate content (which does not contribute an overall acid neutralizing effect) of mine overburden from the alkaline earth metal carbonates that do have acid neutralizing potential. The present invention allows for a better prediction of the quality of mine drainage since it does not overestimate the neutralization potential in cases where transition metal carbonates are present in the mine overburden. This overestimation occurs in conventional ABA methods where the total carbonate content is used to calculate the neutralization potential.

Figure 9:
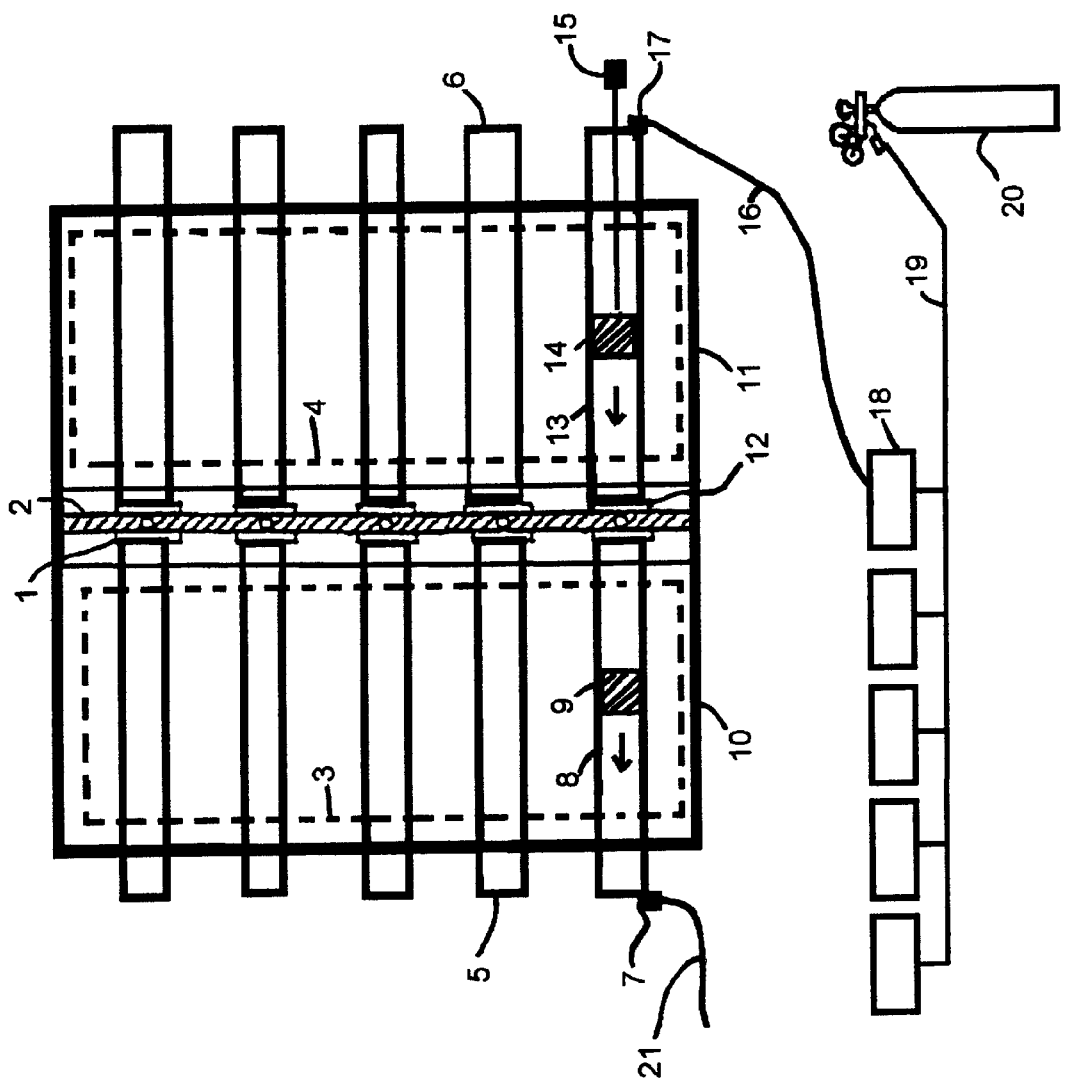
FIG. 9 shows a sample analysis system schematic of the present invention.

FIG. 9 shows a preferred form of a sample furnace for completing the thermal decomposition overburden tests. Plural tube connectors 1 are shown for catalyst tubes in the furnace catalyst hot zone. An insulated wall 2 divides the hot zones. The outline of the heated hot zones is shown in 3 and 4. Plural quartz catalyst tubes (five in this example) are present 5 along with plural quartz sample tubes 6. These are shown positioned against the plural tube connectors. These tubes are held in place by spring loaded plural end connectors (not shown). The oxidation/decomposition gases exit the hot zone through the end connector housing, 7, and move through plural heated lines 21 to a gas analysis system such as an FTIR, mass spectrometer or other gas analysis instrumentation. Gas flow 8 through the catalyst tube is shown as well as catalyst 9 positioned in the tube. The two furnace hot zone cases are shown as 10 and 11. Plural sample tube connectors are shown in 12. Gas flow through the sample tube 13, is shown along with a sample positioned at 14. A thermocouple embedded in the sample is shown in 15. Connecting tube 16 provides for the gas flow to be transferred from plural mass flow meters 18 to inlet housing 17 attached to spring loaded plural end connectors (not shown). Connecting tube 19 provides for transfer of an oxygen-inert gas mixture from a cylinder 20 to plural mass flow meters 18. Alternatively, the appropriate oxygen-inert gas mixture can be obtained by blending gas streams from a cylinder of oxygen and a cylinder of inert gas and using two flow meters for each sample tube. However, this is a less cost effective option.

Figure 10:
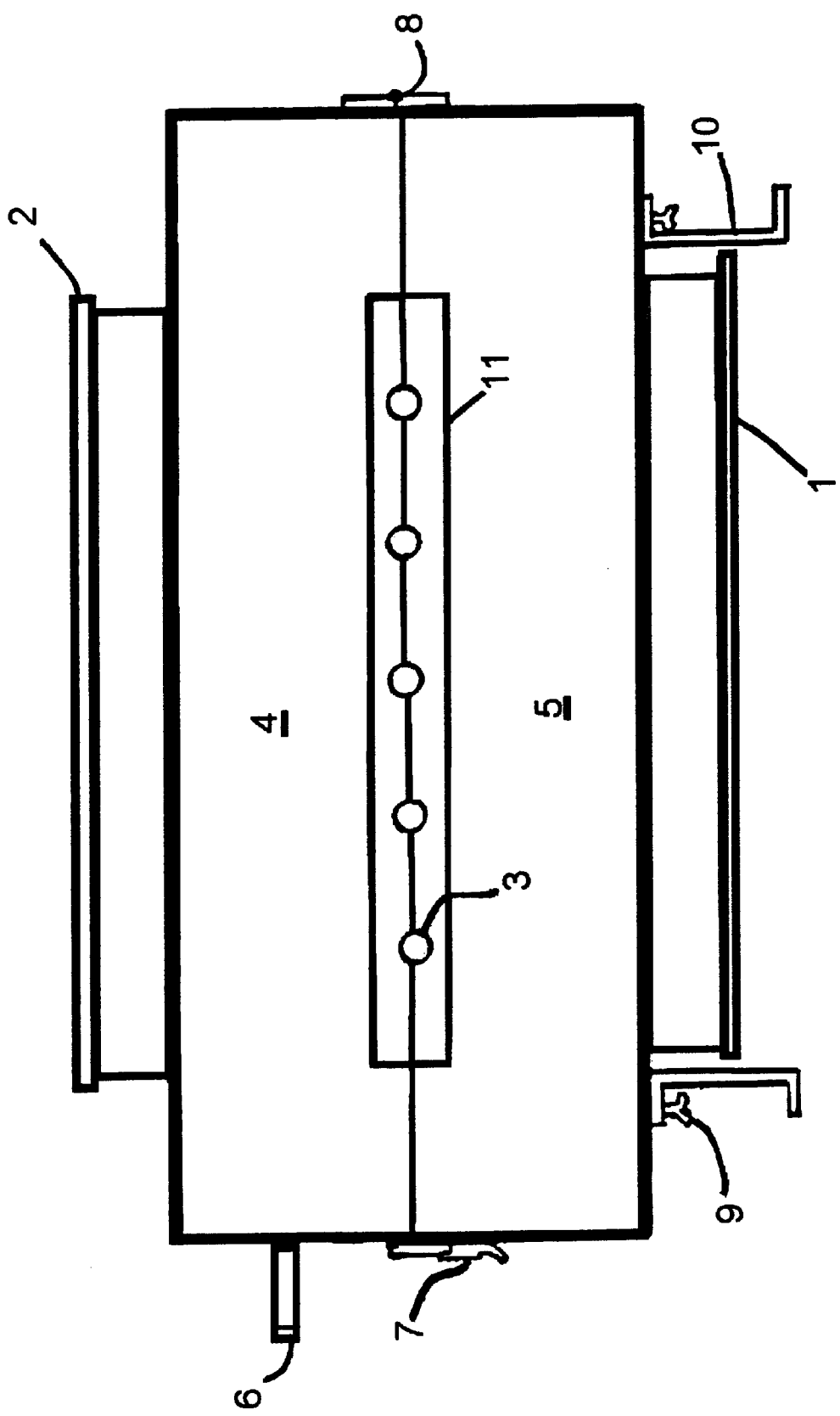
FIG. 10 shows the side elevation of the furnace box.

FIG. 10 shows an end view of a preferred form of a furnace housing. The top half 4 and bottom half 5 open through latch 7 and hinges 8 using handle 6. Identical thermocouple and heater connection housings are shown for the bottom portion of the furnace 1 and the top portion of the furnace 2. The furnace can be repositioned to replace internal thermocouples or heaters located in the lower furnace housing by removing plural fasteners 9. The furnace is held in position by plural mounting brackets 10. Plural openings in the insulated wall on both sides of each hot zone of the furnace 3 provide for the quartz sample and catalyst tubes to extend through the hot zones for attachment to plural tube connectors. Each hot zone contains one heated void 11 through which all of the sample or catalyst tubes extend. The temperature of each of the two hot zone voids 11, in the example shown, contain five sample tubes and each hot zone is controlled by a separate controller.

Figure 11:
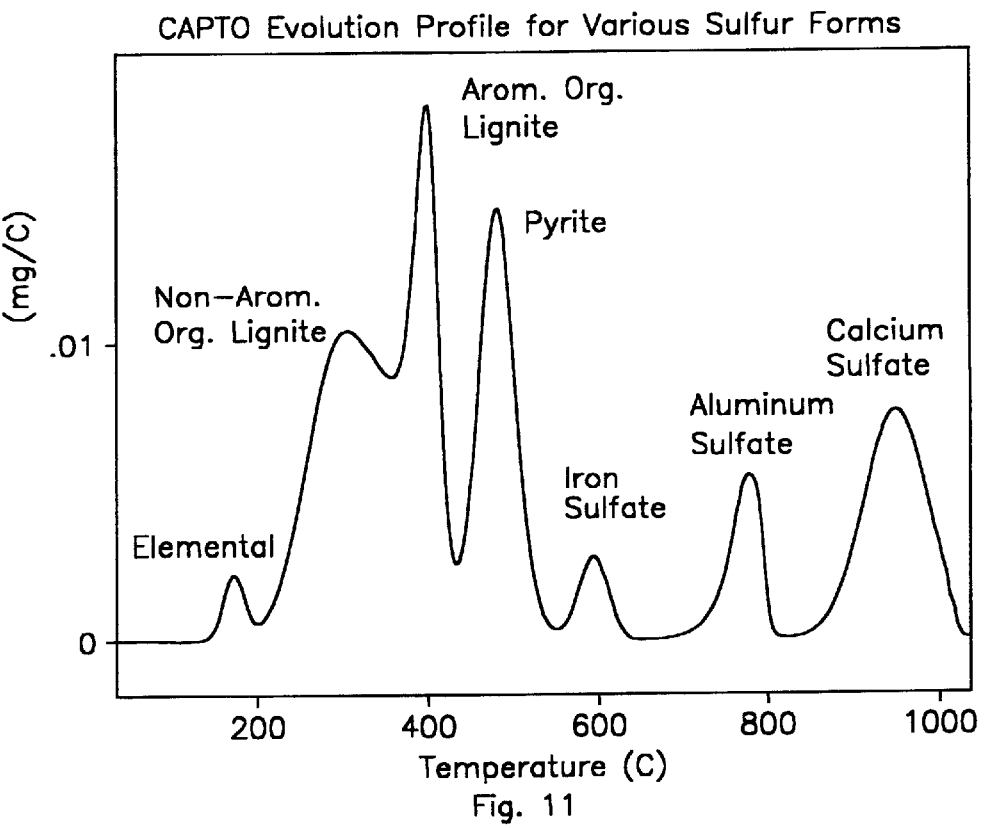
FIG. 11 shows a composite of various sulfur forms detected in coal and coal mineral matter using CAPTO.

FIG. 11 shows a composite of a number of sulfur forms detected and quantitatively determined in coal and coal mineral matter using CAPTO. Many of these same sulfur forms are present in some mine overburdens and will require quantitative analysis using conditions suitable for analysis of carbonates. The conditions used for analysis of the overburdens shown in FIGS. 1–4 are suitable for analysis of these sulfur forms.

Figure 12:
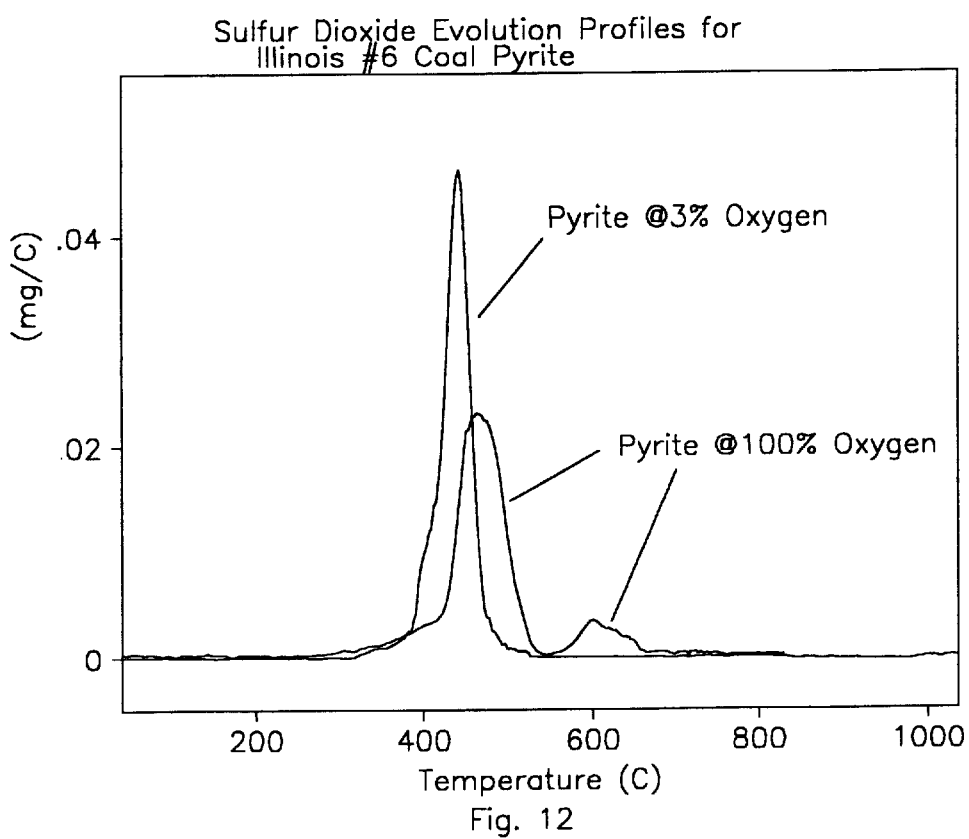
FIG. 12 shows the oxidation temperatures of a coal pyrite oxidized using different oxygen-inert gas concentrations.

FIG. 12 shows both a significant change in profile shape and a shift in pyrite oxidation temperature to lower temperatures as the oxygen concentration is decreased. This type of information may often be used to better separate the oxidation temperatures of pyrite and organic sulfur or other sulfur compounds.

Figure 13:
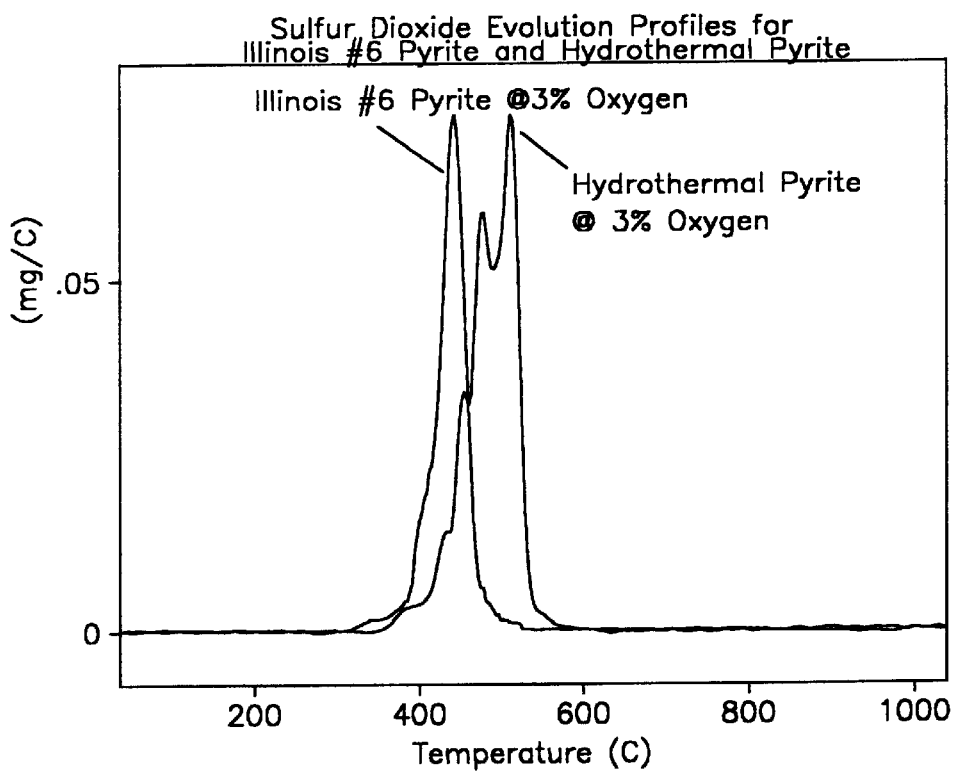
FIG. 13 compares the oxidation temperatures of two different pyrites oxidized under the same oxygen-inert gas conditions.

FIG. 13 compares two different types of pyrite under the same oxidation conditions (3% oxygen). Coal pyrite oxidizes at a significantly lower temperature than the more stable hydrothermal pyrite. Thus, the temperature-programmed thermal analysis of overburdens may provide information on both the amount of pyrite present as well the stability of the pyrite present. Less stable pyrites produce an acidic leach over a shorter period of time than a more stable pyrite. This type of information is not available from the acid/base accounting method currently in use.

Figure 14:
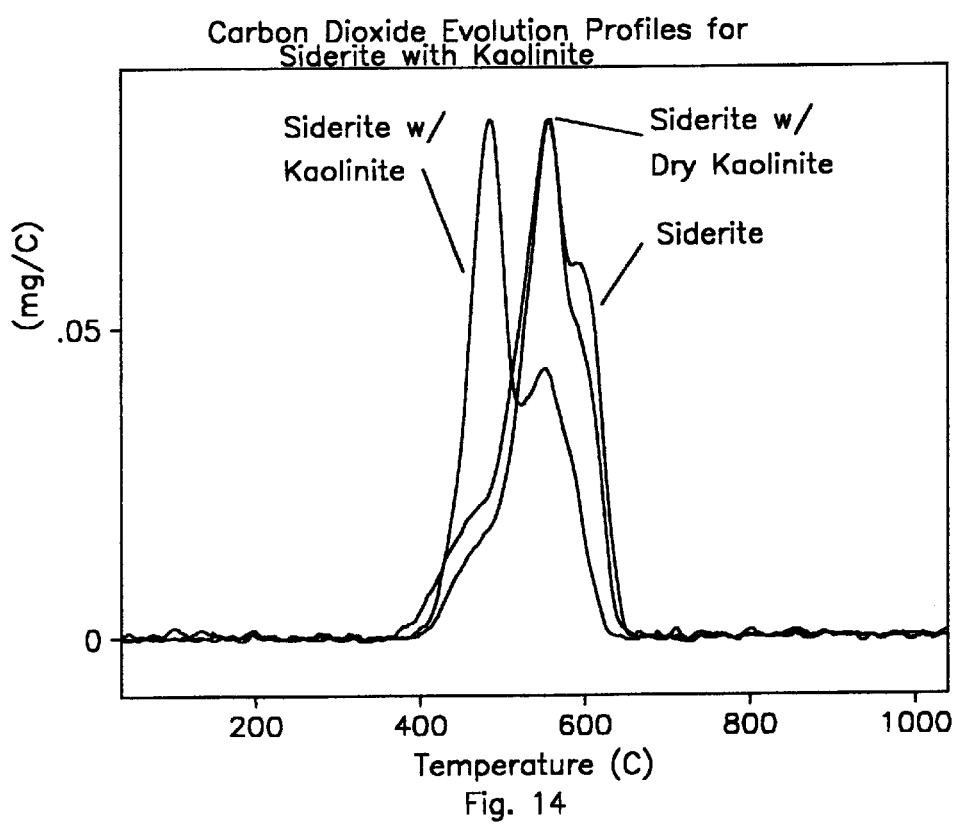
FIG. 14 compares the decomposition temperature profiles for siderite, siderite mixed with kaolinite, and siderite mixed with heat treated (800° C.) kaolinite.

FIG. 14 provides insight required to control the decomposition temperature of siderite in overburden samples that may contain little or no clay. The temperature-programmed thermal analysis profiles of samples of siderite and siderite mixed with heat treated kaolinite (water removed) have similar decomposition temperatures and similar profile shapes. However, the profile produced from siderite that had been mixed with kaolinite (water retained) is strikingly different in both shape, and primary temperature evolution maximum. Note also that the carbon dioxide evolution returns to baseline at a lower temperature than in the other two cases producing a better separation between the decomposition temperatures of siderite and, for example, calcite or dolomite which decompose at a higher temperature than siderite.

Figure 15:
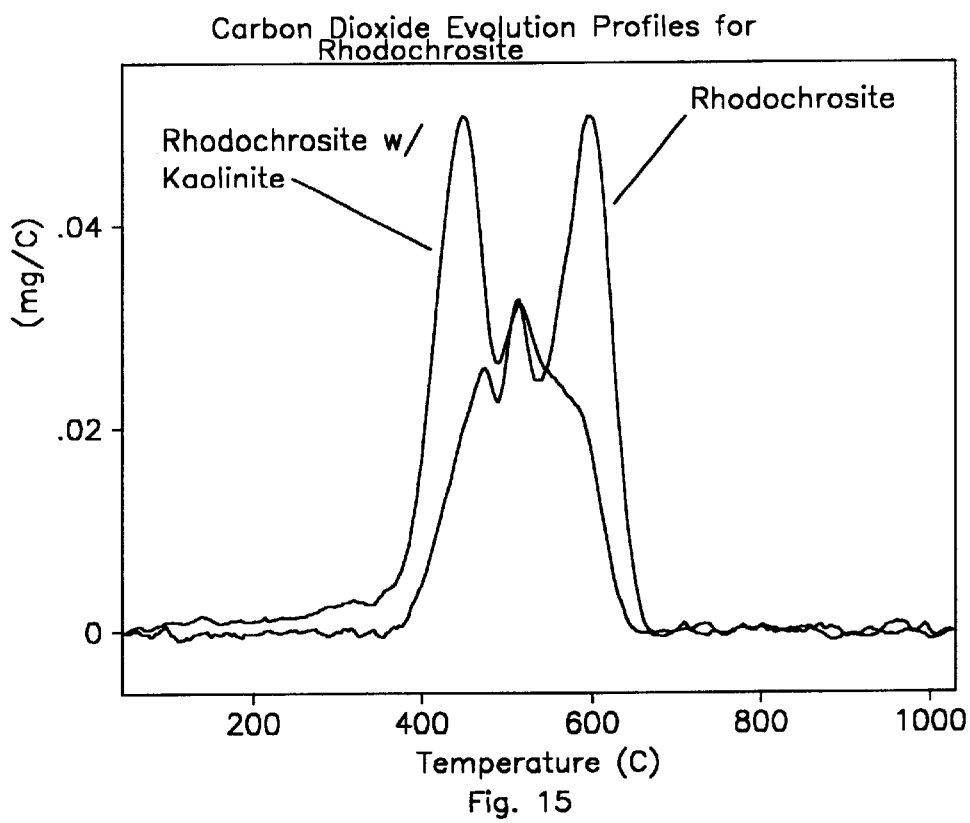
FIG. 15 compares the decomposition temperature of rhodochrosite with rhodochrosite mixed with kaolinite.

FIG. 15 compares the temperature-programmed thermal analysis carbon dioxide profile of rhodochrosite with that of rhodochrosite that had been mixed with kaolinite prior to analysis. Note that the profile produced from the sample of rhodochrosite mixed with kaolinite is strikingly different from that obtained without added kaolinite. The carbon dioxide also returns to baseline at a lower temperature in the profile obtained from the rhodochrosite/kaolinite mixture producing a better separation between rhodochrosite and, for example, calcite or dolomite, which decompose at a higher temperature than rhodochrosite.

The methodology demonstrated in FIGS. 14 and 15 enables one to obtain better separation between the decomposition temperatures of transition metal carbonates such as siderite and rhodochrosite and alkaline earth carbonates such as calcite and dolomite in overburden and other earth samples that contain little or no clay.

Figure 16:
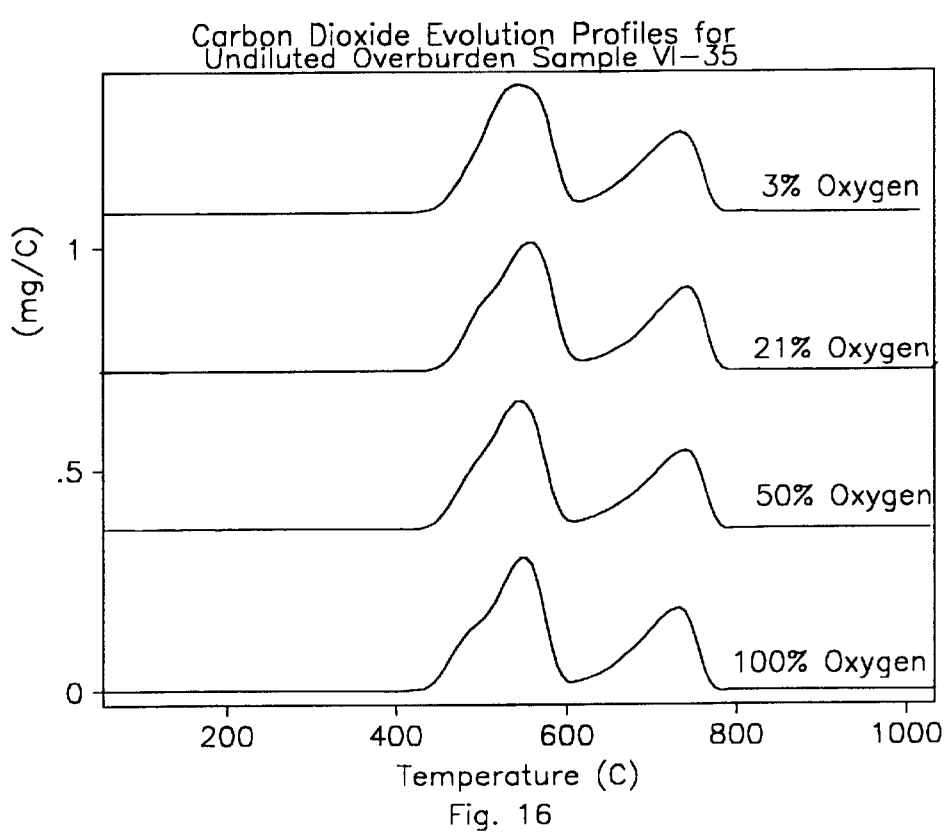
FIG. 16 compares the carbon dioxide profiles of overburden sample VI-35 analyzed without diluent at various oxygen concentrations.

FIG. 16 compares the temperature-programmed thermal analysis carbon dioxide profiles of overburden sample VI-35 (which contains kaolinite) obtained when different concentrations of oxygen are used to complete the analysis. This figure illustrates that some overburden samples containing kaolinite (or other materials that release water, but not interfering gases such as sulfur dioxide or carbon dioxide, over a broad temperature range) can be successfully analyzed using oxygen concentrations ranging from the typically used 3% level up to 100%. Although the higher oxygen concentrations do show a somewhat different shape for the lower temperature evolution (transition metal carbonates) compared to the alkaline earth carbonates, the resolution between the two peaks is sufficient to offer a good quantitative evaluation of each of the two types of carbonates. However, for a general method where some or many samples may not contain kaolinite or other suitable moisture releasing matter, either a low concentration of oxygen is required for analysis, or addition of kaolinite or other suitable substance to the sample prior to analysis is required. A low concentration of water vapor added to the oxidant being flowed through the sample during the analysis is also a suitable alternative. If matter such as kaolinite is not present, a low concentration of oxygen such as 3% would be required for quantitative analysis of mixtures of transition metal carbonates and alkaline earth carbonates as FIGS. 5–8 illustrate.

Overburden sample VI-35 contains no organic carbonaceous matter requiring dilution to avoid exotherms during the analysis. Thus, for the comparisons shown in FIG. 16, the overburden sample was used undiluted to illustrate the observations that when little or no organic carbonaceous matter is present a diluent may be omitted. However, for a general method where some overburden samples contain organic carbonaceous matter, a diluent should be used to reduce or eliminate exotherms that will cause higher temperature evolutions to evolve prematurely along with the evolutions appearing earlier in the thermal analysis.

Figure 17:
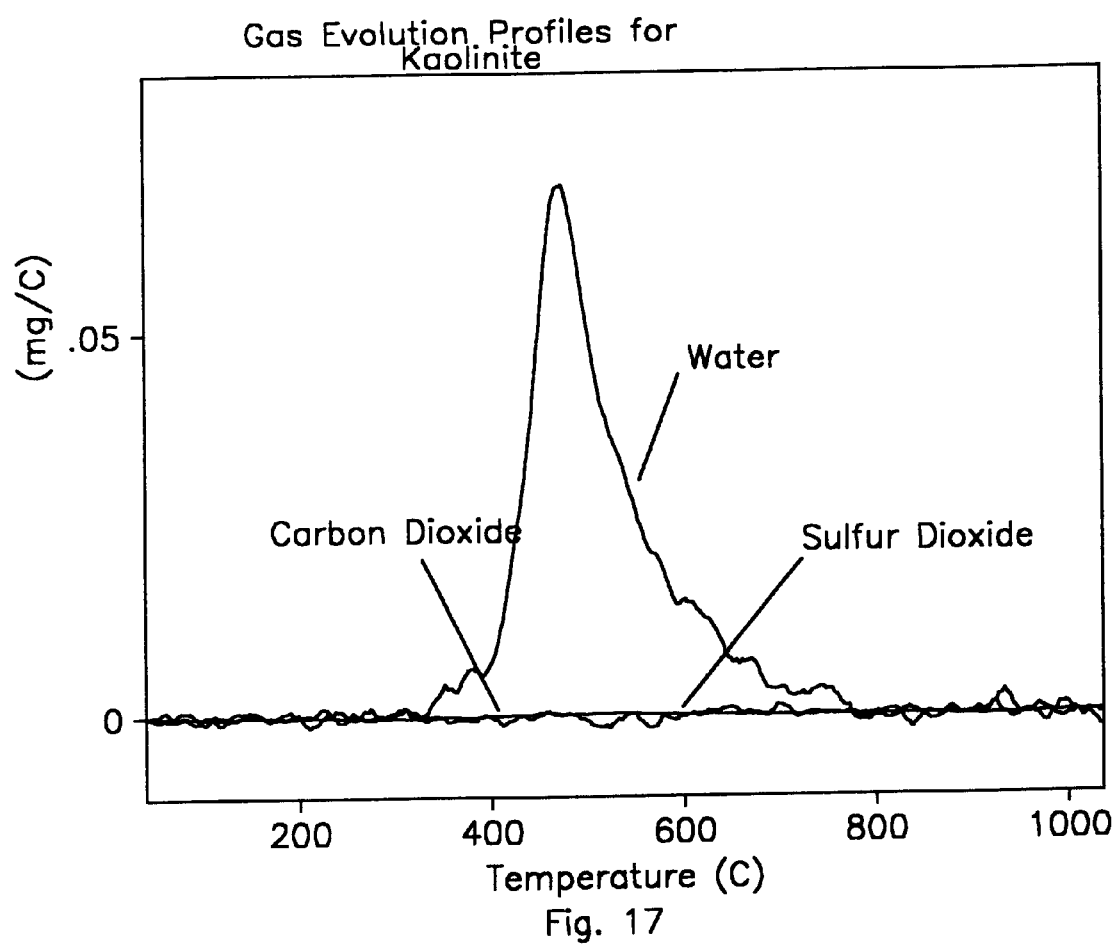
FIG. 17 shows the gas evolution profiles of kaolinite upon temperature-programmed thermal analysis from room temperature to 1050° C.

FIG. 17 shows the gas evolution profiles for a 0.500 g sample of kaolinite as the sample is temperature-programmed from room temperature to 1050° C. Note that no interfering carbon dioxide or sulfur dioxide evolutions are present. The water evolution profile shows that water begins to evolve at about 330° C., reaches a maximum at about 472° C., and continues to evolve until about 770° C. Note that this temperature evolution range includes the temperature range where both the transition metal and alkaline earth metal carbonates thermally react or decompose to evolve carbon dioxide.

Many metal sulfates, sulfides, and carbonates may be quantitatively distinguished by simultaneously using certain controlled atmosphere and thermal conditions attainable with CAPTO. Some of these constituents are present in mine overburden material and must be individually analyzed to obtain a realistic prediction of post mining acid mine drainage problems. Currently, acid base accounting (ABA) analyses are based on the total sulfur and total carbonate content. The present ABA overburden analysis methods can provide erroneous results since, some sulfur forms do not produce acidity upon leaching and some carbonates do not contribute to overall alkalinity. Development of ABA methodology that will also deal with these issues is likely to result in a high volume of service work.

The invention provides a thermal method to analyze, within one working day, mine overburden material for leachable acid/base content.

Existing needs and opportunities are addressed by the new technology. The majority of all new mines developed in the United States are required to have a permit to ensure that acid mine drainage will not become an environmental problem associated with the new mine.

The current methods for overburden acid base accounting (ABA) involve (1) analysis for total alkalinity by titration of total carbonate content and total acidity typically based on total sulfur content, or (2) actual leaching over many weeks (ten plus) to obtain the acid leach potential. The second analysis in some states is seldom recommended due to the cost, and the fact that no standard leach method or extensive data base is available.

An improved method is required. The current ABA method can provide erroneous results since, some sulfur forms do not produce acidity upon leaching and some carbonates do not contribute to overall alkalinity. Despite considerable work to improve overburden testing procedures, no standard or routine method has emerged that provides reliable predictions of acid mine drainage from all overburdens in a cost effective manner. The current methods can predict post-mine drainage quality when the acid potential or neutralization potential clearly predominates. However, there remains a "grey" area where current techniques often fail to accurately predict post-mining water quality. Therefore, no mines are permitted if the ABA is within the "grey" area. The inaccuracy in the wet chemical ABA predictive technique prevents the opening of mines that may not generate an acid discharge. This loss of mining opportunity translates to loss of jobs and the other economic advantages that accompany mining.

Scientists at the Federal Energy Technology Center (FETC) are interested in a thermal analytical method as a route to improve overburden analyses. Using thermal analysis equipment they completed research toward such a method. A one-step thermal ABA method was not realized due to the lack of selectivity in decomposition temperatures among metal carbonates under conditions suitable for analysis of metal sulfides. The capability to distinguish among metal carbonates present in overburden samples is important since all carbonates do not contribute to overall alkalinity.

The present invention has developed a thermal route that selectively decomposes mixtures of the two primary carbonate groups (alkaline earth metal and transition metal carbonates) present in many bituminous coal overburden samples. One of these carbonate groups contributes to overall alkalinity of overburden leach, while the other does not. Work with several mine overburden samples confirms the selective decomposition results. The invention provides a viable method for prediction of the neutralization potential and the maximum potential acidity of overburdens.

Previous work resulted in development of a Controlled-Atmosphere Programmed-Temperature Oxidation (CAPTO) instrument/method for use as a tool to facilitate (a) analyses of treated coals, (b) new coal upgrading technologies under study, and (c) solutions to challenging analytical problems that arise in the coal and a variety of other industries. For example, the previous work resulted in patented methodology for determination of the sulfur forms in coal and coal mineral matter. These are the same sulfur forms that must be determined in order to accurately predict the acid leach potential of the overburden.

The new technology fits well with technology previously developed for determination of sulfur forms. That technology combined with current successes for thermal analysis of carbonates leads to an improved one-step ABA method for overburden analyses and a better prediction of post acid mine drainage.

Patented thermal methods are already in place to accurately account for the sulfur forms in coal and the mineral matter found with coal. These sulfur forms include elemental sulfur; organic sulfur; pyrite; iron sulfate; jarosites; and sodium, potassium, aluminum, magnesium and calcium sulfates. Oxidation/decomposition of a number of these sulfur forms is shown in FIG. 11. Several of these sulfur forms may be present in overburden samples and must be determined for a precise accounting of the overburden acidity. Conversely, forms such as some organic sulfur, magnesium sulfate, and calcium sulfate do not contribute to overburden acidity and should not be counted as contributing toward acid mine drainage.

The thermal oxidation temperature maximum of pyrite correlates with the ease of weathering of the pyrite. The lower the thermal oxidation temperature the more readily pyrite in the overburden will weather (oxidize) and produce acid. Information of this type is not available from the current wet chemical ABA methodology.

The thermal/controlled atmosphere methodology for sulfur forms determination is fully developed. However, for a one-step ABA characterization, conditions must be found suitable for characterization of both the sulfur forms and the metal carbonates. The 3% oxygen in inert gas and 3–10° C. temperature ramp used in the thermal analysis of overburden samples examined are suitable for analyzing the sulfur forms and transition metal/alkaline earth metal carbonates in a one-step method. Further studies related to oxygen concentration and temperature ramp have now been completed. If water vapor is present during the analysis, higher oxygen concentrations can be utilized. Temperature ramp may be in the 3–10° C. range or higher if desired.

A strong continuing interest in improving overburden analysis methods led to new initiatives toward a one-step thermal analytical method for overburden analysis. Preliminary experiments using a variety of thermal/controlled atmosphere conditions with several metal carbonates and various sulfides/sulfates were completed. Synthetic samples of metal carbonates were selectively decomposed using conditions also suitable for oxidation of sulfur forms. The present invention provides an inexpensive method for predicting the likelihood of acid discharge from proposed mines. Using one determination per sample, the invention provides a method to identify and quantify the sulfur and carbonate containing minerals in mine overburdens to predict the likelihood of post acid mine drainage.

Understanding the characteristics of thermal oxidation/decomposition of the actual sulfides/sulfates-carbonates present in overburden leads to a good prediction of the acidic/alkaline weathering potential of strata. This invention permits a more accurate prediction of acidic mine drainage in the overburden compared to predictions based on total sulfur/carbonate and enables mine operators to plan their mining and reclamation operations accordingly. The test results for acid discharge potential that now accompany new mine permit applications may overestimate or underestimate the acidic discharge potential of the overburden.

All carbonate and sulfur forms cannot be expected to leach. The total carbonate neutralizing capacity of an overburden sample that contains both iron carbonate (siderite) and calcium carbonate (calcite) will not be realized in an actual leaching experiment since only the calcium carbonate readily leaches. The hydrolysis of iron in dissolved siderite generates acid that neutralizes the carbonate alkalinity. Siderite either does not dissolve, or if it does, it does not contribute to acidity or alkalinity. Likewise, if an overburden that contains pyrite, iron sulfate, and calcium sulfate is analyzed for sulfur content and related to acidity, the potential acidity will be overestimated since calcium sulfate does not contribute to acidity.

If the total inorganic sulfur content and, therefore, the potential acidity is higher than the neutralization potential of an overburden, a mining permit will not be issued. However, if much of the sulfur is present as calcium sulfate only a fraction of the potential acidity will be realized and the mine could possibly have been permitted. Similarly, if the potential basicity is greater than the potential acidity a mining permit may be issued. However, if much of the carbonate present occurs as iron carbonate, a mine acid drainage problem may still arise since the carbonate neutralization potential from iron carbonate will not be realized.

The new thermal analytical route provides improved overburden analysis. The thermal analytical method to improve overburden analyses is based on the following key points:

(a) Identifying any changes in thermal decomposition behavior of metal carbonates and oxidation/decomposition of sulfur forms with variation in the gas or gas composition passing through the sample as the sample is heated at a constant or variable rate from some lower temperature to beyond it's decomposition point.

(b) Identifying any changes in thermal decomposition behavior of metal carbonates and decomposition or oxidation behavior of sulfur forms present in the analysis samples with the addition of a substance (to the sample that does not contain interfering sulfur forms or carbonates but itself) or through a different substance that it produces/releases insitu as the sample is heated at a constant or variable rate from some lower temperature to beyond the decomposition/oxidation points of the components to be analyzed.

(c) Identifying gas compositions and the proper temperatures for changing gas compositions (if required) consistent with obtaining well resolved sulfur dioxide evolutions produced from metal sulfides, sulfates, and hydroxy sulfates found in the overburden samples is required. A knowledge of the thermal decomposition/oxidation behavior of metal sulfides, the thermal decomposition of metal sulfates, and any hydroxy sulfates present in overburden samples is required. This same information with respect to variation in the gas or gas composition passing through the sample as it is heated through the same temperature regime is required.

For example, iron hydroxy sulfates (jarosites) decompose to produce sulfur dioxide above 500° C. under oxidation conditions but show no sulfur dioxide evolution up to 1050° C. under inert gas conditions. If the sample previously exposed to inert gas conditions up to 1050° C. is treated again under oxidizing conditions, the characteristic decomposition and sulfur dioxide evolution above 500° C. is not observed. Thus, oxidizing conditions are required to obtain a reliable estimate of some sulfur forms through a thermal oxidation/decomposition procedure. Similar but not identical considerations are encountered with pyrite under pyrolysis and oxidation conditions. The thermal method may require changes in gas or gas composition throughout the temperature regime if both sulfur forms and carbonate are to be reliably determined from one determination.

(d) Identifying gas compositions and/or the proper temperatures for changing gas compositions in order to obtain well resolved carbon dioxide evolutions produced from transition metal and alkaline earth metal carbonates present in the overburden samples is required for a successful method. For example, the carbon dioxide evolutions produced from siderite and calcite decomposition in air occur as severely overlapping peaks. This overlap of the carbon dioxide evolutions from the metal carbonates makes quantitative determinations difficult and non-reproducible and has deterred development of a one-step thermal analytical method for analysis of these carbonates. However, a thermal study of siderite and calcite under differing gas concentrations shows variation in decomposition temperatures and permits a quantitative thermal analytical method to be utilized at least for the analysis of synthetic mixtures and the overburden samples examined to date.

Siderite, rhodochrosite, calcite, and dolomite are the primary carbonates present in bituminous coal mine overburden. Under certain thermal/controlled atmosphere conditions siderite and rhodochrosite decompose to produce a carbon dioxide evolution in a peak resolved from that produced by calcite or dolomite. This provides an effective route to eliminate siderite and rodochrosite from the neutralization potential of the overburden.

Gas switching and gas concentration variation may be used to selectively, thermally decompose carbonate mixtures. Previous examination of the thermal oxidation/decomposition of sulfides/sulfates using a variety of oxygen/inert gas concentrations revealed a trend of pyrite to oxidize at lower temperature as the oxygen concentration decreased. Use of this information coupled with the current determinations of the thermal behavior of siderite, rhodochrosite, calcite, dolomite and the sulfates using a variety of controlled atmosphere conditions permits a thermal, one-step, direct determination of the acidity/basicity likely to result in the leachate from an overburden sample.

The four key points (a, b, c and d noted above) are useful for synthetic mixtures of sulfur forms and carbonates found in coal mine overburdens. Specifically, a known quantity of sample mixture is mixed with a diluent inert to these components and placed in a quartz combustion tube. This tube is placed in a furnace designed to provide a constant temperature throughout the sample region. Plug flow of a gas or precise gas mixture and temperature ramp are under computer control. The oxidation/decomposition gases pass through a second furnace held at 1050° C. (to maintain constant gas equilibria of the evolved gases and constant temperature of the gases entering the analysis cell) and through heated lines to a sample cell positioned in the sample compartment of a Fourier Transform infrared Spectrometer (FTIR). Both the temperature of the gas evolution and the quantity of each gas evolved are measured, and the data is saved to a computer file. From this data the evolution temperature and the type and amount of gas from each component is calculated.

The invention provides complete thermal/controlled atmosphere studies of synthetic mixtures of the metal sulfides/sulfates and metal carbonates found in coal mine overburden as well as for actual mine overburdens that may or may not contain a clay such as kaolinite.

These composites are characterized using a variety of controlled atmosphere and temperature ramp conditions to establish optimum conditions for the ABA methodology.

Using the optimum conditions established, the composites are characterized using variation in sample size to establish the minimum detection limits for each component.

The invention formalizes and automates data reporting procedures for the experimental conditions established.

Overburden samples vary in composition and collection site. These samples include cases where acid mine drainage is expected, unlikely, and in the unknown or "grey" area.

Thermal results are compared with ABA results completed using one of the conventional wet chemical ABA procedures. Further work may involve thermal testing of the residue of partially leached overburden samples. This work identifies the acid and base producing components most susceptible to leaching from overburdens and enables a better prediction of leach acidity/alkalinity with amount of leachate or time. The construction of low cost multiple-sample prototype thermal instrumentation is specifically designed to minimize the cost of overburden analysis.

The invention provides a totally new approach to ABA for bituminous coal mine overburdens. Although similar ABA issues are encountered in the hard rock mining industry, the initial thrust is directed toward bituminous coal mine overburdens related to the development of surface mines.

The current fee structure from one testing service for the conventional tests (sample preparation, fizz rating, neutralization potential, total sulfur and sulfur forms) is $41.20 per sample or $361,530 per year just for Pennsylvania surface mining. Most coal analysis or environmental testing laboratories offer these tests. This appears to be a cost effective method; however, the test results obtained may not provide a good prediction of mine acid discharge. This is particularly true if considerable iron carbonate (siderite) or calcium sulfate (gypsum) is present. This knowledge coupled with the fact that no "standard" ABA method has emerged, despite considerable effort, indicates that development of an improved ABA method accepted by state and federal agencies will significantly impact this market.

Most coal analysis and environmental laboratories throughout Pennsylvania, the neighboring Appalachian states and the nation offer conventional ABA testing. However, if a new, thermal method for overburden analysis were recommended by the state Departments of Environment and the Office of Surface Mining to the coal industry, the new method will be used.

EXAMPLE

Sample Size

Approximately 0.500 g of a dry representative overburden sample of −60 Mesh or smaller is used in an analysis; however, the sample size could vary from 0.050 g up to 1 g or more, depending upon the concentration of the components that are to be analyzed in the overburden sample.

Sample Diluent

Depending on the concentration of the components in the overburden to be analyzed the diluent could range from 0 to 12 g. A diluent is typically used to minimize sample matrix effects, promote oxidation, and to dilute any carbonaceous material that may be present in the sample in order to avoid exotherms. Since the majority of overburden samples have little carbonaceous material present, the danger of an exotherm occurring in these samples is minimized. Typical diluents are, for example, but not limited to, tungsten trioxide, zirconium oxide, sand, silicates, and other silica products, as well as other materials inert to the components being analyzed and the gases evolved.

Use of Kaolinite

Kaolinite (typically, about 0.500 g) can be added to the sample. This permits any concentration of oxygen desired to be used in the analysis and still retain good resolution between the decomposition temperatures of the transition metal and alkaline earth metal carbonates.

Sample Analysis Tube

The diluted sample is positioned in a quartz sample tube between quartz wool retainers. A solid quartz rod is positioned in the tube using quartz wool retainers. This rod occupies space to reduce system "dead volume". The sample tube is positioned (spring loaded) in a specially designed furnace and heated at one or more linear rates throughout the experiment (typically 3–10° C./minute). The maximum sample temperature may vary from 1050–1200° C. depending on the overburden sample matrix. The sulfates, particularly those not contributing to overburden acidity such as magnesium sulfate and calcium sulfate may be shifted to a higher evolution temperature (i.e., the peak maximum for calcium sulfate may increase from 950° C. to 1050° C. requiring a higher ramp temperature and the use of ceramic sample tubes if the temperature is increased above 1150° C.) The evolved gases move through the sample tube into a combustion tube containing tungsten trioxide catalyst held at 1050° C. to insure a constant temperature and gas equilibrium of the exiting gases. The gases, for analysis, pass through heated lines to a specially designed gas cell positioned in the sample compartment of a Fourier Transform Infrared Spectrophotometer.

Gas Type/Concentration in Use for Overburden Analysis

The gas concentration now in use for analysis of overburden samples is 3% oxygen in 97% inert gas (Argon). Nitrogen can be used as the "inert" gas. This gas concentration provides adequate separation of the decomposition temperatures for the transition metal carbonates (rhodochrosite-manganese carbonate and siderite-iron carbonate) from the alkaline earth metal carbonates (calcite-calcium carbonate and dolomite-calcium magnesium carbonate) that are present in the overburden samples. The oxygen concentration used could change somewhat as a wider range of overburden samples are explored. Intermittent steps of an oxygen concentration range of from 0 to 100% have been explored for overburden samples. While a typical value of 3% oxygen is now used, values as high as 100% oxygen may be used in special cases where samples contain large amounts of organic matter or clays such as kaolinite. The higher concentration of oxygen will decrease the oxidation temperature of the organic material and if a substance such as kaolinite is present will still provide good separation between the decomposition (reaction) temperatures of the transition metal and alkaline earth metal carbonates. This higher oxygen concentration can prove useful in these special cases to clearly distinguish between oxidation of organic carbon and decomposition of transition metal carbonates.

Thermocouple

A type K thermocouple is embedded in the sample diluent mixture for observation of the sample temperature throughout the determination. A platinum rhodium alloy thermocouple is used if the temperature ramp is to continue above 1150° C.

A Typical Analysis Procedure

A 0.500 g representative sample of an overburden of particle size −60 mesh or smaller is diluted with 6 g of sand (acid washed and heat treated to 1100° C.) and positioned in a quartz combustion tube between quartz wool plugs. A quartz rod spacer is positioned on one end and held in place by a quartz wool plug. The tube is inserted between spring loaded gas inlet outlet seals as a type K thermocouple is positioned in the sample. A quartz tube containing 12 g of tungsten trioxide is positioned in a secondary furnace and heated at 1050° C. throughout the sample tube temperature ramp.

Plug flow of 100 ml/minute of a 3% oxygen/97% argon gas mixture is passed through the sample as the temperature is increased at a rate of 3–10° C./minute. A typically rate of up to 7° C./minute is used if the overburden sample does not contain a black carbon color indicating significant carbon content. If considerable organic carbon is present, a rate of 3–5° C./minute is used to avoid exotherms produced from the heat released as the organic carbon is oxidized. Evolved gases from the sample pass through the catalyst tube and through heated lines to a gas analysis cell positioned in the cell compartment of a Fourier Transform Infrared spectrometer. The temperature of the sample is increased to at least 1050° C. (1150° C. in sample series where matrix effects shifts sulfates to higher temperatures and calcium sulfate evolves above 950° C.). If a ceramic sample tube is used the temperature ramp may be continued up to 1200° C. or higher.

Temperature data and evolved gas analysis data are stored in computer files throughout the temperature ramp and analyzed at the completion of the run. On-the-fly profiles are observed on the computer monitor as the run progresses. The amount and temperature profile of each gas evolved is reported.

While the invention has been described with reference to specific embodiments, modifications and variations of the invention may be constructed without departing from the scope of the invention, which is defined in the following claims.

I claim:

1. A mine overburdens analysis method comprising providing a sample, treating the sample with different concentrations of oxygen in inert gas, varying heat temperatures corresponding to the concentrations of the oxygen in the inert gas, thereby differing decomposition rates of substances in the mine overburdens, detecting the different decomposition rates of the substances, and analyzing the substances present in the mine overburdens.

2. The method of claim 1, wherein the detecting comprises detecting substances comprising alkaline earth metal carbonates.

3. The method of claim 1, wherein the detecting comprises detecting substances comprising transition metal carbonates.

4. The method of claim 1, wherein the treating comprises supplying concentrations of the oxygen sufficient for optimal thermal decomposition of components of the substances.

5. The method of claim 1, wherein the differing decomposition rates comprises supplying concentrations of oxygen sufficient for allowing thermal decomposition of alkaline earth metal carbonates.

6. The method of claim 1, wherein the substances comprise alkaline earth metal carbonates and transition metal carbonates.

7. The method of claim 1, wherein the differing decomposition rates comprises supplying concentrations of oxygen sufficient for allowing thermal decomposition of transition metal carbonates.

8. The method of claim 6, wherein the alkaline earth metal carbonates comprise calcite, dolomite and the transition metal carbonates comprise rhodochrosite and siderite.

9. The method of claim 1, wherein the differing decomposition rates comprises supplying concentrations of oxygen sufficient for separating components of the substances.

10. The method of claim 1, wherein the differing decomposition rates further comprises differing decomposition of the mine overburdens for forming differently decomposed substances comprising transition metal carbonates, alkaline earth carbonates, and sulfur compounds using controlled concentrations of oxygen, and analyzing the differently decomposed substances.

11. The method of claim 1, wherein the oxygen-inert gas comprises about 3% oxygen in inert gas.

12. The method of claim 11, wherein the inert gas is selected from a group consisting of nitrogen, argon, and other inert gases.

13. The method of claim 1, wherein concentration of oxygen in the oxygen-inert gas is in a range from about 0% to 10%.

14. The method of claim 13, wherein concentration of oxygen in the oxygen-inert gas is in a range from about 0% to 5%.

15. The method of claim 10, wherein the analyzing comprises selective analysis of the carbonates wherein the alkaline earth metal carbonates content have an overall acid neutralizing effect, measuring the neutralizing effect, and computing the transition metal carbonate content of the mine overburdens from the alkaline earth metal carbonates content, thereby preventing overestimation of neutralization of mine drainage.

16. The method of claim 1, wherein the analyzing comprises detecting sulfur forms and the analyzing comprises quantitatively determining sulfur forms in the mine overburdens.

17. The method of claim 1, wherein the analyzing comprises detecting and analyzing pyrites at temperatures corresponding decreasing oxygen concentrations.

18. The method of claim 17, wherein the analyzing pyrites comprises analyzing coal pyrites oxidized at first temperatures and analyzing hydrothermal pyrites oxidized at second temperatures wherein the first temperatures for analyzing the coal pyrites is lower than the second temperatures for analyzing the hydrothermal pyrites.

19. The method of claim 18, wherein the analyzing comprises determining a quantity and a stability rating of the pyrites.

20. The method of claim 3, wherein the detecting comprises detecting transition metal carbonates in the overburdens comprising clay.

21. The method of claim 1, wherein the detecting and the analyzing comprises identifying any changes in thermal decomposition rates of metal carbonates corresponding to a variation in the treating with different concentrations of the gas and the heating at a constant or variable rate from a lower temperature to beyond decomposition points of substances in the overburdens.

22. The method of claim 1, wherein the detecting and analyzing comprises identifying any changes in thermal decomposition of metal carbonates and decomposition or oxidation of sulfur present in the samples in presence of a substance added to the overburdens or a substance produced insitu on heating the sample at a constant or variable rate from a lower temperature to beyond decomposition points of overburden components to be analyzed.

23. The method of claim 1, wherein the treating with different concentrations comprises identifying appropriate gas compositions and corresponding temperatures for changing gas compositions consistent with obtaining well resolved sulfur dioxide evolutions produced from metal sulfides, sulfates, and hydroxy sulfates in the overburden samples.

24. The method of claim 1, further comprising decomposition and oxidation of the substances, comparing the detected decomposition and oxidation rates of the substances in the sample with predetermined decomposition rates and concentrations thereby predicting concentrations of the substances.

25. The method of claim 1, further comprising identifying gas compositions and/or proper temperatures for changing gas compositions to obtain well resolved carbon dioxide evolutions produced from metal carbonates present in the overburden samples under the different gas concentrations thereby indicating variation in decomposition rates, and analyzing by a quantitative thermal analytical method thereby predicting in a thermal, one-step, direct determination the acidity/basicity in leachates from the overburdens.

26. The method of claim 1, further comprising mixing water vapor with the treating gas to form a mixture and treating the sample with the mixture.

* * * * *